United States Patent
Campins et al.

(10) Patent No.: US 8,450,311 B2
(45) Date of Patent: May 28, 2013

(54) PHARMACEUTICAL COMPOSITIONS CONTAINING A FLUOROQUINOLONE ANTIBIOTIC DRUG

(75) Inventors: Inmaculada Campins, Mataró (ES); Nuria Jiménez, Barcelona (ES); Roman Vidal, Vallromanes (ES); Nuria Carreras, Caldes de Montbui (ES); Carmen Martinez, Lliçà de Vall (ES); Francisco Javier Galán, Teià (ES)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/474,307

(22) Filed: May 29, 2009

(65) Prior Publication Data

US 2009/0306128 A1 Dec. 10, 2009

Related U.S. Application Data

(60) Provisional application No. 61/059,877, filed on Jun. 9, 2008.

(51) Int. Cl.
*A61K 31/535* (2006.01)
*A61K 33/14* (2006.01)

(52) U.S. Cl.
USPC ........ 514/230.2; 514/780; 514/782; 514/947; 424/675; 424/678

(58) Field of Classification Search
USPC .............. 514/230.2, 780, 782, 947; 424/675, 424/678
See application file for complete search history.

(56) References Cited

U.S. PATENT DOCUMENTS

| | | | |
|---|---|---|---|
| 4,136,177 | A | 1/1979 | Lin et al. |
| 6,143,799 | A | 11/2000 | Chowhan et al. |
| 6,166,012 | A | 12/2000 | Muller et al. |
| 6,174,524 | B1 | 1/2001 | Bawa et al. |
| 6,261,547 | B1 | 7/2001 | Bawa et al. |
| 6,331,540 | B1 | 12/2001 | Kabra |
| 6,352,978 | B1 | 3/2002 | Perdiguer et al. |
| 6,716,830 | B2 | 4/2004 | Cagle et al. |
| 7,795,316 | B1 | 9/2010 | Kabra |
| 2001/0049366 | A1 | 12/2001 | Singh et al. |
| 2010/0035894 | A1 | 2/2010 | Sawa |
| 2011/0117189 | A1 | 5/2011 | Mazzone et al. |

FOREIGN PATENT DOCUMENTS

| | | |
|---|---|---|
| CA | 2 666 440 | 4/2008 |
| EP | 2078526 | 7/2009 |
| EP | 2078527 | 7/2009 |
| WO | 93/21903 | 11/1993 |
| WO | 00/18386 | 4/2000 |
| WO | 2008/044733 | 4/2008 |
| WO | 2008/044734 | 4/2008 |

OTHER PUBLICATIONS

Annick Ludwig, "The use of mucoadhesive polymers in ocular drug delivery", University of Antwerp, Belgium, 2005.
International Search Report of a related PCT Application No. PCT/US2009/045549, mailed Jul. 29, 2009.
International Written Opinion of a related PCT Application No. PCT/US2009/045549, mailed Jul. 29, 2009.
Corresponding PCT/US2009/045549 International Preliminary Report on Patentability dated Aug. 20, 2010.

*Primary Examiner* — Zohreh Fay
(74) *Attorney, Agent, or Firm* — Scott A. Chapple

(57) ABSTRACT

Pharmaceutical compositions containing a fluoroquinolone antibiotic drug are disclosed. The compositions exhibit improved homogeneity, improved bioavailability, lower turbidity or a combination thereof. The composition can be use as otic or nasal compositions, but are particularly useful as ophthalmic compositions.

17 Claims, 2 Drawing Sheets

PHARMACEUTICAL COMPOSITIONS CONTAINING A FLUOROQUINOLONE ANTIBIOTIC DRUG

CROSS-REFERENCE TO RELATED APPLICATION

The present application claims priority based on U.S. Provisional Patent Application Ser. No. 61/059,877 filed Jun. 9, 2008.

FIELD OF THE INVENTION

The present invention relates to pharmaceutical compositions. In particular, this invention relates to pharmaceutical compositions that include a fluoroquinolone antibiotic drug in a pharmaceutical vehicle that provides improved homogeneity, improved bioavailability, lower turbidity or a combination thereof.

BACKGROUND OF THE INVENTION

Fluoroquinolone antibiotic drugs have exhibited efficacy in a variety of pharmaceutical applications. Of particular importance to the present invention, fluoroquinolone antibiotic drugs have exhibited efficacy in ophthalmic, nasal and otic pharmaceutical compositions for treating conditions such as conjuctivitis. However, fluoroquinolone antibiotic drugs, particularly moxifloxacin, can have characteristics that create difficulties in designing pharmaceutical vehicles suitable for delivery of the drugs.

As one example, many fluoroquinolones can cause turbidity when used in pharmaceutical solutions, particularly viscous aqueous solutions (e.g., aqueous ophthalmic multi-dose solutions). As a further example, many fluoroquinolones, particularly hydrophobic fluoroquinolones, tend to exhibit less bioavailability in such solutions. Still further, many fluoroquinolones, again particularly hydrophobic fluoroquinolones, exhibit a distinct lack of homogeneity in such solutions.

Previous research efforts have uncovered ingredients useful in addressing the difficulties of designing pharmaceutical vehicles for fluoroquinolones. As one example, U.S. Pat. No. 6,331,540, which is fully incorporated herein by reference for all purposes, discusses the advantages of using xanthan gum as part of a pharmaceutical vehicle for a fluoroquinolone such as ciprofloxacin.

Such discoveries, while quite desirable, still leave drawbacks and difficulties in formulating pharmaceutical vehicles for fluoroquinolones. As such, the present invention provides pharmaceutical vehicles for a fluoroquinolone drug or pharmaceutical compositions that include a fluoroquinolone drug where the vehicle or composition exhibits improved homogeneity, improved bioavailability, lower turbidity or any combination thereof.

SUMMARY OF THE INVENTION

Therefore, the present invention is direct to a pharmaceutical vehicle and a pharmaceutical composition including that vehicle. The pharmaceutical composition includes a fluoroquinolone antibiotic drug. The pharmaceutical vehicle typically includes one or more of the following: i) sodium chloride in an amount that provides a weight/volume ratio of sodium chloride to the fluoroquinolone drug that is between 0.8 and 2.0; ii) a surfactant that promotes the homogeneity of the composition and/or assists in evenly distributing the fluoroquinolone drug throughout the pharmaceutical vehicle; and/or a borate/polyol complex antimicrobial system.

The pharmaceutical composition can be an ophthalmic aqueous solution. The pharmaceutical composition can also be located within a container that dispenses the composition as drops. In a preferred embodiment, the fluoroquinolone drug includes or is substantially entirely moxifloxacin. It is also contemplated that the weight/volume ratio of sodium chloride to the fluoroquinolone drug can be between 1.0 and 1.7 and more preferably between 1.1 and 1.4. The vehicle of the composition can further comprise a viscosity enhancing agent such as xanthan gum. It is also contemplated that the pharmaceutical vehicle can consist essentially of sodium chloride, borate/polyol system, xanthan gum, surfactant, sodium hydroxide and purified water. The composition, the vehicle or both may also exhibit a pH of 6.8 to 7.4.

BRIEF DESCRIPTION OF THE DRAWINGS

The accompanying drawings, which are incorporated in and constitute a part of this specification, illustrate aspects of the invention and together with the description, serve to explain the principles of the invention.

DETAILED DESCRIPTION OF THE INVENTION

Figure 1:
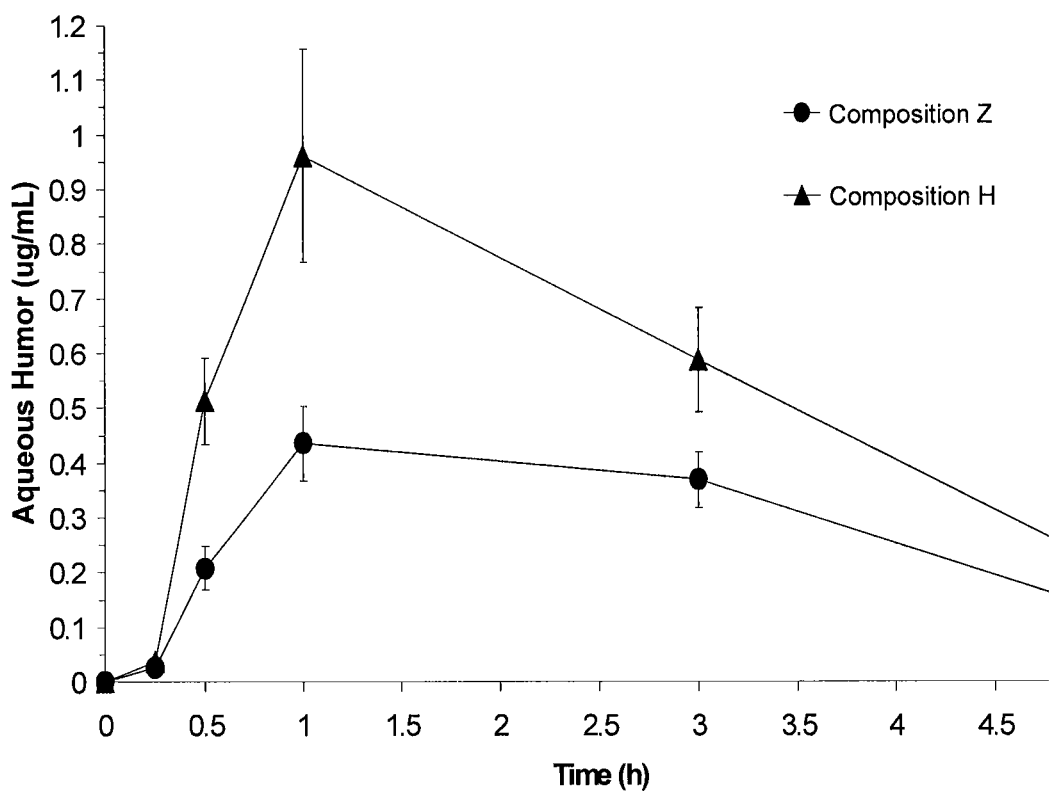
FIG. 1 is a graph of the concentration of fluoroquinolone in the aqueous humor of human eyes after doses of a composition according to the present invention and after doses of a composition with a marketed product having the same fluoroquinolone.

Unless otherwise indicated, all ingredient concentrations are listed as weight volume (w/v) percentages (%).

The amount of fluoroquinolone drug included in the compositions of the present invention can be any amount that is therapeutically effective and will depend upon a number of factors, including the identity and potency of the chosen drug. The total concentration of fluoroquinolone drug in the composition will generally be about 1.5% or less. In topically administrable ophthalmic compositions, the typical concentration of fluoroquinolone drug (e.g., moxifloxacin) will be at least about 0.2%, more typically at least about 0.4% and possibly at least about 0.5% but will typically be less than about 2.0% more typically less than about 1.0% and still more typically less than about 0.7%.

Potentially suitable fluoroquinolones include, without limitation, ciprofloxacin, moxifloxacin, levofloxacin, enrofloxacin, ofloxacin, gatifloxacin and norfloxacin. The fluoroquinolone drug can include a single fluoroquinolone or a combination of multiple different fluoroquinolones. Further, it shall be understood that, for the present invention, the naming of a particular fluoroquinolone is considered to include salts and derivatives of that fluoroquinolone, unless otherwise specifically stated. For example, the name moxifloxacin is meant to include moxifloxacin, moxifloxacin HCl and derivatives of moxifloxacin.

Moxifloxacin is a particularly preferred fluoroquinolone drug. Thus, in a preferred embodiment, the fluoroquinolone drug can be at least 50%, more typically at least 70% and even more typically at least 90% by weight moxifloxacin. Of course, in this embodiment, the fluoroquinolone drug can be substantially entirely or entirely moxifloxacin.

As use herein, the term substantially as it is used to modify terms such as entirely is intended to mean all but a nominal amount.

The composition and/or vehicles of the present invention also typically include viscosity enhancing agent. Various ingredients, particularly polymer or hydrocarbons, can be employed for the viscosity enhancing agent and the viscosity enhancing agent can include one or multiple ingredients. The viscosity enhancing agent is typically at least 0.1%, more typically at least 0.3% and even more typically at least 0.6% of the composition and/or vehicle of the present invention. The viscosity enhancing agent is typically less than 4.0%, more typically less than 1.2% and even more typically less than 0.75% of the composition and/or vehicle of the present invention.

Polysaccharide and particularly xanthan gum is desirable as the viscosity enhancing agent. Thus, in a preferred embodiment, the viscosity enhancing agent can be at least 50%, more typically at least 70% and even more typically at least 90% by weight polysaccharide and, more particularly, xanthan gum. Of course, in this embodiment, the viscosity enhancing agent can be substantially entirely or entirely polysaccharide and, in particular, xanthan gum.

Xanthan gum is generally available in at least two grades from some commercial suppliers, a food or industrial grade and a pharmaceutical grade. When used, it is preferable to polish filter even pharmaceutical grade materials so that the finished pharmaceutical product will have increased clarity. As one skilled in the art appreciates, the appropriate filter size for polish filtration depends upon the size of the undesired impurities contained in raw material. For example, in the case of a solution composition, it has been found that the Rhodigel Clear grade of xanthan gum from Rhone-Poulenc Inc. should be filtered through a 0.45 μm filter in order to remove cell debris and impurities. Multiple stages of filters can be used to increase the overall efficiency of the polish filtration process.

The composition and/or vehicle of the present invention can also include an antimicrobial system such as a borate/polyol complex system. An example of one potentially suitable system is discussed in U.S. Pat. No. 6,143,799, which is incorporated herein by reference for all purposes.

As used herein, the term "borate" shall refer to boric acid, salts of boric acid, borate derivatives and other pharmaceutically acceptable borates, or combinations thereof. Most suitable are: boric acid, sodium borate, potassium borate, calcium borate, magnesium borate, manganese borate, and other such borate salts. Borate interacts with polyols, such as glycerol, propylene glycol, sorbitol and mannitol, to form borate polyol complexes. The type and ratio of such complexes depends on the number of OH groups of a polyol on adjacent carbon atoms that are not in trans configuration relative to each other. It shall be understood that weight/volume percentages of the ingredients polyol and borate include those amounts whether as part of a complex or not.

As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol, sorbitol and propylene glycol. In one embodiment, the polyol of the borate/polyol system is at least 70% by weight, more particularly at least 90% by weight, substantially entirely or entirely mannitol, sorbitol or a combination thereof.

When used, the borate/polyol complex antimicrobial system (i.e., the borate and polyol together) is typically at least 0.03 w/v %, more typically at least 0.2 w/v % and even possibly at least 0.5 w/v % of the composition, the vehicle or both. When used, the borate/polyol complex antimicrobial system is typically less than 3 w/v %, more typically less than 1 w/v % and even possibly less than 0.7 w/v % of the vehicle, the composition or both.

The compositions and/or vehicles of the present invention typically include halide and, more particularly non-hydrogen halide salt that preferably improves clarity of the composition and/or vehicle. As used herein, non-hydrogen halides include all halides with the exception of hydrogen halides such hydrogen chloride (HCl) where hydrogen provide the positive charge of the halide that matches the negative charge of the halogen. It is contemplated that the non-hydrogen halide or halide salt may include a single halide or may be composed of multiple different halides. The non-hydrogen halide or halide salt is typically at least 0.1 w/v %, more typically at least 0.4 w/v % and even possibly at least 0.5 w/v % and even more possibly at least 0.65 w/v % of the composition, the vehicle or both. The halide or halide salt is typically less than 3 w/v %, more typically less than 1.5 w/v % and even possibly less than 1.0 w/v % of the vehicle, the composition or both.

Suitable non-hydrogen halides (e.g., halide salts) include, without limitation, sodium chloride, potassium chloride, calcium chloride, combinations thereof or the like. While it is contemplated that the non-hydrogen halide of the present invention can be formed of multiple different ingredients, it has advantageously been found that sodium chloride (NaCl) alone or substantially alone can provide a highly desired reduction in nephelos or turbidity of the composition and/or vehicle without the need for other non-hydrogen halides. Thus, it is contemplated that the composition and/or vehicle of the present invention is entirely or substantially free of any non-hydrogen halide other than NaCl.

To achieve desirably low levels of turbidity, it is preferable to have particular ratios for the w/v % of non-hydrogen halide in the composition relative to w/v % of fluoroquinolone drug in the composition. Such ratio is typically between 0.7 and 2.2, more typically between 1.0 and 1.7 and still more typically between 1.1 and 1.4. These ratios have been shown to be of particular importance for the combination of moxifloxacin with NaCl in the presence of xanthan gum.

The turbidity of the composition, the vehicle or both is desirably low when measured in nephelometric turbidity units (NTUs) according to European Standard EN ISO 7027: 1999. The turbidity of the composition, the vehicle or both is typically less than 20 NTU, more typically less than 13 NTU, still more typically less than 10 NTU and even possibly less than 8 NTU. Visual clarity is preferably less than or equal to ($\leqq$) PIII, more preferably $\leqq$PII and still more preferably $\leqq$PI according to Chapter 2.2.1 of the European Pharmacopeia, $6^{th}$ edition.

The composition and/or vehicle solubility of the present invention can include surfactant or other appropriate co-solvent. The surfactant may be nonionic, anionic, cationic, amphoteric, or amphiphilic. Exemplary nonionic surfactants or co-solvents include tyloxapol, polyoxyethylene sorbitan esters, polyethoxylated castor oils, polyethoxylated hydrogenated castor oils such as HCO-40, poloxamers, polyoxyethylene/polyoxypropylene surfactants, polyoxyethylene lauryl ether, polyoxyethylene stearate, polyoxyethylene propylene glycol stearate, hydroxyalkylphosphonate, a combination thereof, or other agents known to those skilled in the art.

The surfactant, when included, is typically at least 0.005 w/v %, more typically at least 0.02 w/v % and even possibly at least 0.04 w/v % of the composition, the vehicle or both. The surfactant, when included, is also typically less than 1 w/v %, more typically less than 0.1 w/v % and even possibly less than 0.07 w/v % of the vehicle, the composition or both.

Polyether alcohol (e.g., alkyl aryl polyether alcohol) surfactants have been found to be particularly useful in the vehicles and compositions of the present invention. Such surfactants have been found to assist in dispersing the fluoroquinolone drug, particularly moxifloxacin, throughout the composition such that the overall composition has greater homogeneity. This is particularly important when the composition is a multi-dose solution (e.g., ophthalmic solution) that is located within a container (e.g., a dropper) and is administered in drop form. The greater homogeneity can provide for more uniform amounts of drug to be administered in each drop. This is particularly the case where the surfactant promotes homogeneity in the tip of the dropper and it has been found that the surfactants discussed herein, particularly alkyl aryl polyether alcohol such as tyloxapol, have been found to facilitate greater homogeneity at the dropper tips. Thus, it is contemplated that the surfactant can be at least 50%, more typically at least 70% and even more typically at least 90% by weight polyether alcohol (e.g., alkyl aryl polyether alcohol such as tyloxapol). Of course, in this embodiment, the surfactant can be substantially entirely or entirely polyether alcohol (e.g., alkyl aryl polyether alcohol such as tyloxapol).

In addition to the ingredients above, it is contemplated that a variety of additional or alternative ingredients may be employed in the compositions or vehicles of the present invention. Other additional therapeutic agents, antimicrobials, suspension agents or the like may be included. Other exemplary ingredients possible for the composition or vehicle include, without limitation, tonicity agents, buffering agents, anti-oxidants, combinations thereof or the like. Water will make up a substantial portion of the aqueous solutions as will become apparent from the examples below. Hydrochloric acid, sodium hydroxide or other acids or bases may be used to adjust pH.

The ingredients described herein may be used in forming various types of pharmaceutical compositions or vehicles such as ophthalmic, otic, nasal and dermatological compositions or vehicles, but are particularly useful for ophthalmic solutions, which are typically aqueous. Examples of such solutions include, without limitation, ophthalmic pharmaceutical topical solutions that can be used in the treatment of glaucoma, dry eye, infections, allergies or inflammation (e.g., conjunctivitis); solutions for enhancing the ocular comfort of patients; and various other types of ophthalmic solutions, such as ocular lubricating products, artificial tears, astringents, and so on.

The compositions or vehicles of the present invention are typically formulated so as to be compatible with the eye and/or other tissues to be treated therewith. The ophthalmic compositions or vehicles intended for direct application to the eye will be formulated so as to have a pH and tonicity that are compatible with the eye.

The compositions will typically have a pH in the range of 4 to 9, preferably 5.5 to 8.5, and most preferably 5.5 to 8.0. Particularly desired pH ranges are 6.0 to 7.8 and more specifically 6.4 or even 6.7 to 7.5 or even 7.2. The compositions will have an osmolality of 200 to 400 or 450 milliosmoles per kilogram (mOsm/kg), more preferably 240 to 360 mOsm/kg.

It is typically preferable for the compositions or vehicles of the present invention to have sufficient antimicrobial activity to allow them to satisfy the certain preservative efficacy requirements, particularly USP preservative efficacy requirements and/or Ph. Eur. B.

The preservative efficacy standards for multi-dose ophthalmic solutions in the U.S. and other countries/regions are set forth in the following table:

Preservative Efficacy Test ("PET") Criteria Log Order Reduction of Microbial Inoculum Over Time

|  | Bacteria | Fungi |
|---|---|---|
| USP 27 | A reduction of 1 log (90%), by day 7; 3 logs (99.9%) by day 14; and no increase after day 14 | The compositions must demonstrate over the entire test period, which means no increases of 0.5 logs or greater, relative to the initial inoculum. |
| Japan | 3 logs by 14 days; and no increase from day 14 through day 28. | No increase from initial count at 14 and 28 days |
| Ph. Eur. A[1] | A reduction of 2 logs (99%) by 6 hours; 3 logs by 24 hours; and no recovery after 28 days | A reduction of 2 logs (99%) by 7 days, and no increase thereafter |
| Ph. Eur. B | A reduction of 1 log at 24 hours; 3 logs by day 7; and no increase thereafter | A reduction of 1 log (90%) by day 14, and no increase thereafter |
| FDA/ISO 14730 | A reduction of 3 logs from initial challenge at day 14; and a reduction of 3 logs from rechallenge | No increase higher than the initial value at day 14, and no increase higher than the day 14 rechallenge count through day 28. |

[1]There are two preservative efficacy standards in the European Pharmacopoeia "A" and "B".

The standards identified above for the USP 27 are substantially identical to the requirements set forth in prior editions of the USP, particularly USP 24, USP 25 and USP 26.

In at least several embodiments of the present invention, it has been found that the overall composition or vehicle can provide a desired bioavailability without the need for inclusion of additional ingredients. Thus, it is contemplated that the vehicle may consist or consist essentially of only the following: viscosity enhancing agent; borate/polyol system; surfactant; non-hydrogen halide; sodium hydroxide or hydrochloric acid; and water or any combination thereof as those ingredients are described herein. Further it is contemplated in such embodiment that the composition may consist of or consist essentially of only the following: fluoroquinolone drug; viscosity enhancing agent; borate/polyol system; surfactant; non-hydrogen halide; sodium hydroxide or hydrochloric acid; and water or any combination thereof as those ingredients are described herein.

The following examples are presented to illustrate further various aspects of the present invention, but are not intended to limit the scope of the invention in any respect.

EXAMPLES

Each of the formulations shown in Tables 1 and 2 below was prepared as follows. Xanthan gum stock solution was prepared and clarified through 1.2 and 4.5 μm filters. Sodium chloride was added to and dissolved in the xanthan gum to form a xanthan gum solution. If present, boric acid, sorbitol, tyloxapol and moxifloxacin were combined with purified water to form a second solution. All ingredients of the second solution were dissolved by stirring and pH was adjusted by adding NaOH or HCl. Then the second solution was added into the xanthan gum solution and the formulation was mixed by stirring until obtaining a substantially homogeneous solution. Purified water was added up to final volume to form the final solution, which was mixed again by stirring. The final solution was then autoclaved at 124° C. for 40 minutes. The sterilized final solution was then cooled to room temperature. If necessary, pH was adjusted again by adding NaOH or HCl and sterilized purified water is added up to final volume. The final solution was mixed by stirring to homogenize.

TABLE 1

| Ingredients | % (w/v) | | | | | |
|---|---|---|---|---|---|---|
| | A | B | C | D | E | F |
| Moxifloxacin HCl | 0.545 | 0.545 | 0.545 | 0.545 | 0.545 | 0.545 |
| Xanthan Gum | 0.6 | 0.6 | 0.6 | 0.6 | 0.6 | 0.6 |
| Boric acid | 0.4 | 0.4 | 0.3 | 0.4 | 0.3 | 0.4 |
| Tyloxapol | 0.05 | 0.05 | — | 0.05 | 0.05 | 0.05 |
| Sorbitol | 0.2 | 0.2 | — | 0.2 | 0.2 | 0.2 |
| Sodium chloride | 0.5 | 0.58 | 0.64 | 0.64 | 0.7 | 0.7 |
| Sodium hydroxide | pH 6.8 | pH 6.8 | pH 6.8 | pH 6.8 | pH 6.8 | pH 6.8 |
| Purified water | q.s. | q.s. | q.s. | q.s. | q.s. | q.s. |
| Turbidity (NTU) | 47 | 23 | 39 | 18 | 8 | 7 |
| Clarity (Ref. Susp. Ph. Eur.) | >PIV | PIII | PIV | PII-PIII | PI | <PI |
| pH | 6.7 | 6.8 | 6.8 | 6.8 | 6.8 | 6.8 |

TABLE 2

| Ingredients | % (w/v) | | | | |
|---|---|---|---|---|---|
| | F | G | H | I | J |
| Moxifloxacin HCl | 0.545 | 0.545 | 0.545 | 0.545 | 0.545 |
| Xanthan Gum | 0.6 | 0.6 | 0.6 | 0.6 | 0.4 |
| Boric acid | 0.4 | 0.3 | 0.3 | 0.3 | 0.3 |
| Tyloxapol | 0.05 | 0.05 | 0.05 | — | 0.05 |
| Sorbitol | 0.2 | 0.2 | 0.2 | — | 0.2 |
| Sodium chloride | 0.7 | 0.7 | 0.7 | 0.7 | 0.7 |
| Sodium hydroxide | pH 6.8 | pH 7.0 | pH 7.4 | pH 7.4 | pH 7.4 |
| Purified water | q.s. | q.s. | q.s. | q.s. | q.s. |
| Turbidity (NTU) | 7 | 6 | 6 | 7 | 4 |

TABLE 2-continued

| Ingredients | % (w/v) | | | | |
|---|---|---|---|---|---|
| | F | G | H | I | J |
| Clarity (Ref. Susp. Ph. Eur.) | <PI | <PI | PI | PI | PI |
| pH | 6.8 | 7.0 | 7.3 | 7.4 | 7.5 |

It has also been found that compositions of the present invention provide higher concentrations of fluoroquinolone drug, particularly moxifloxacin to a biological target (e.g., the eye) at later times after administering the composition to the target. For example, a composition substantially identical to composition H from table 2 was applied to the eyes of rabbits and the following concentrations were observed in the aqueous humor and tear film of the eyes of those rabbits:

Mean Concentration±SD of Moxifloxacin in Tear Film Following Administration of Composition

| Sampling time (min) | Concentration (μg/mL) |
|---|---|
| 1 | 3656 ± 1292 |
| 5 | 2035 ± 273 |
| 10 | 122 ± 120 |
| 30 | 13.59 ± 9.17 |
| 60 | 4.98 ± 3.99 |

Mean Concentration±SD of Moxifloxacin in Aqueous Humor Following Administration of Composition

| Sampling time (min) | Concentration (μg/mL) |
|---|---|
| 15 | 2.21 ± 0.69 |
| 30 | 4.74 ± 0.70 |
| 60 | 2.54 ± 0.77 |
| 120 | 0.78 ± 0.30 |

Advantageously, these concentrations, particularly after the passing of the 5 minute, 10 minute, 15 minute, 30 minute and 60 minute time intervals, are at least double, triple, 5× or even 8× the concentrations of moxifloxacin composition currently commercially available.

Aqueous humor concentrations of moxifloxacin in micrograms per milliliter (μg/ml) in human eyes at each of 5 collection times are presented in Table 3 below and are graphically shown in FIG. 1. In particular, the table and graph show mean concentrations in the aqueous humor after a single topical dose of a moxifloxacin composition according to the present invention (composition H from above) and after a single topical dose of a commercially available moxifloxacin composition that is available under the tradename VIGAMOX® from Alcon Laboratories, Fort Worth, Tex., 76134. Composition Z is represented by VIGAMOX®, in addition to moxifloxacin hydrochloride, includes boric acid, sodium chloride, and purified water and may also contain hydrochloric acid/sodium hydroxide to adjust pH to approximately 6.8.

TABLE 3

| Time (h) | Composition Z | Composition H |
|---|---|---|
| 0.25 | <0.025$^a$ | 0.0363 |
| 0.5 | 0.208 | 0.513 |
| 1 | 0.435 | 0.961 |
| 3 | 0.368 | 0.588 |
| 5 | 0.135 | 0.223 |

Aqueous humor concentrations of moxifloxacin in micrograms per milliliter (μg/ml) in human eyes at each of 5 collection times are also presented in Table 4 below and are graphically shown in FIG. 2. In particular, the table and graph show mean concentrations in the conjunctival tissue after a single topical dose of composition H and after a single topical dose of VIGAMOX®.

TABLE 4

| Time (h) | Composition Z | Composition H |
|---|---|---|
| 0.25 | 22.3 | 43.8 |
| 0.5 | 24.1 | 35.5 |
| 1 | 8.60 | 19.3 |
| 3 | 1.73 | 2.22 |
| 5 | 1.16 | 1.85 |

Figure 2:
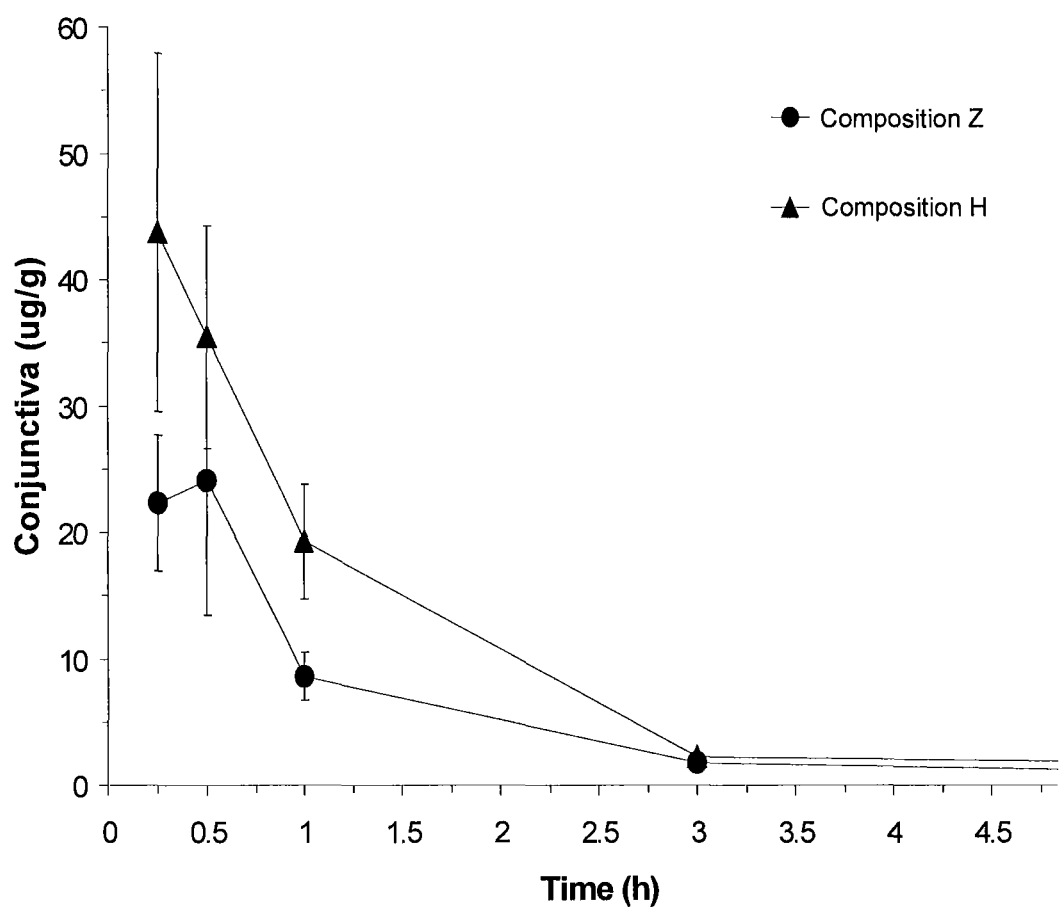
FIG. 2 is a graph of the concentration of fluoroquinolone in the conjunctiva of human eyes after doses of a composition according to the present invention and after doses of a composition with a marketed product having the same fluoroquinolone.

As can be seen from tables 3 and 4 and FIGS. 1 and 2, the compositions of the present invention can provide significantly higher concentrations of moxifloxacin to the aqueous humor and the conjunctival tissue of the human eye.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. An aqueous pharmaceutical composition, comprising:
a fluoroquinolone drug consisting of moxifloxacin in the composition at a concentration that is at least 0.4 w/v % but less than 1.0 w/v %; and
a pharmaceutical vehicle for the fluoroquinolone drug, the pharmaceutical vehicle consisting essentially of:
   i. sodium chloride in an amount that provides a weight/volume ratio of sodium chloride to the fluoroquinolone drug in the composition that is between 1.0 and 1.7;
   ii. a surfactant that assists in evenly distributing the fluoroquinolone drug throughout the pharmaceutical vehicle wherein the surfactant is a polyether alcohol;
   iii. a borate and a polyol;
   iv. a polysaccharide viscosity enhancing agent comprised of xanthan gum in an amount such that the concentration of the xanthan gum in the composition is at least 0.3 w/v % but less than 1.2 w/v % wherein the xanthan gum is at least 90% by weight of the viscosity enhancing agent;
   v. a pH adjusting agent; and
   vi. water;
wherein the composition is an aqueous ophthalmic solution and wherein the composition exhibits turbidity that is less than 13 NTU.

2. A composition as in claim 1 wherein the composition is located within a container that dispenses the composition as drops.

3. A composition as in claim 1 wherein the sodium chloride is in the composition at a concentration such that the weight/volume ratio of sodium chloride to the fluoroquinolone drug that is between 1.1 and 1.4.

4. A composition as in claim 1 wherein the polyol comprises sorbitol.

5. A composition as in claim 1 wherein the viscosity enhancing agent consists of xanthan gum.

6. A composition as in claim 1 wherein the pharmaceutical vehicle consists essentially of sodium chloride, a surfactant, a borate, a polyol, xanthan gum, sodium hydroxide and water.

7. A composition as in claim 1 wherein the composition has a pH of 6.8 to 7.4 and the turbidity is less than 10 NTU.

8. An aqueous pharmaceutical composition, comprising:
a fluoroquinolone drug wherein the fluoroquinolone drug is moxifloxacin at a concentration that is at least 0.4 w/v % but less than 1.0 w/v %; and
a pharmaceutical vehicle for the fluoroquinolone drug, the pharmaceutical vehicle consisting essentially of:
   i. sodium chloride in an amount that provides a weight/volume ratio of sodium chloride to the fluoroquinolone drug in the composition that is between 1.1 and 1.4;
   ii. a surfactant that assists in evenly distributing the fluoroquinolone drug throughout the pharmaceutical vehicle;
   iii. a borate and a polyol; and
   iv. a polysaccharide viscosity enhancing agent comprised of xanthan gum in an amount such that the concentration of the xanthan gum in the composition is at least 0.3 w/v % but is less than 1.2 w/v % wherein the xanthan gum is at least 90% by weight of the viscosity enhancing agent;
   v, a pH adjusting agent; and
   vi, water;
wherein the composition is an aqueous ophthalmic solution and wherein the composition is located within a container that dispenses the composition as drops and wherein the composition exhibits turbidity that is less than 10 NTU.

9. A composition as in claim 8 wherein the composition has a pH of 6.8 to 7.4.

10. A composition as in claim 8 wherein the polysaccharide viscosity enhancing agent consists of xanthan gum.

11. A composition as in claim 8 wherein the surfactant is a polyether alcohol.

12. A composition as in claim 8 wherein the surfactant is an alkyl aryl polyether alcohol.

13. A composition as in claim 12 wherein the polysaccharide viscosity enhancing agent consists of xanthan gum.

14. A composition as in claim 12 wherein the composition has a pH of 6.8 to 7.4.

15. A composition as in claim 1 wherein the surfactant is an alkyl aryl polyether alcohol.

16. An aqueous pharmaceutical composition, comprising:
a fluoroquinolone drug comprised of moxifloxacin in the composition at a concentration that is at least 0.4 w/v % but less than 0.7 w/v %; and
a pharmaceutical vehicle for the fluoroquinolone drug, the pharmaceutical vehicle including the following:
   i. sodium chloride in an amount that provides a weight/volume ratio of sodium chloride to the fluoroquinolone drug in the composition that is between 1.1 and 1.4;
   ii. a surfactant that assists in evenly distributing the fluoroquinolone drug throughout the pharmaceutical vehicle wherein the surfactant is a polyether alcohol;

iii. a borate and a polyol;
iv. a polysaccharide viscosity enhancing agent comprised of xanthan gum in an amount such that the concentration of the xanthan gum in the composition is at least 0.6 w/v % but is less than 0.75 w/v % wherein the xanthan gum is at least 90% by weight of the viscosity enhancing agent;
v. a pH adjusting agent; and
vi. water;

wherein the composition is an aqueous ophthalmic solution and wherein the composition exhibits turbidity that is less than 13 NTU.

17. A composition as in claim 16 wherein the composition has a pH of 6.8 to 7.4 and the turbidity is less than 10 NTU.

* * * * *